United States Patent [19]
Dalise

[11] 4,193,194
[45] Mar. 18, 1980

[54] DENTURE

[76] Inventor: David D. Dalise, Suite A, 7111 Prospect Pl. NE., Albuquerque, N. Mex. 87110

[21] Appl. No.: 916,891

[22] Filed: Jun. 19, 1978

[51] Int. Cl.² .......................................... A61C 13/22
[52] U.S. Cl. .................................................. 433/177
[58] Field of Search ................... 32/5, 6, 7, 12, 13, 32/10 A

[56] References Cited
U.S. PATENT DOCUMENTS

| | | | |
|---|---|---|---|
| 2,112,007 | 3/1938 | Adams | 32/10 A |
| 3,085,334 | 4/1963 | Bischaf et al. | 32/10 A |
| 3,413,721 | 12/1968 | Pickering | 32/2 |
| 3,748,739 | 7/1973 | Thibert | 32/10 A |
| 3,787,975 | 1/1974 | Zuest | 32/5 |

*Primary Examiner*—Robert Peshock
*Attorney, Agent, or Firm*—Donald P. Smith

[57] ABSTRACT

Apparatus for attaching a removable denture to a natural or an implanted fixed root system. The invention embodies a small resilient ring that provides circumferential retention of the denture and the inherent resiliency of the ring enables ease of placement and removal.

8 Claims, 3 Drawing Figures

DENTURE

BACKGROUND OF THE INVENTION (1) Field of the Invention

The invention relates to a method and a structure for attaching a removable denture to a natural or an implanted fixed root system wherein a high degree of circumferential retention of the denture is provided and, in addition, placement and removal of the denture is facilitated.

(2) Description of the Prior Art

Many prior art systems for placing and removal of a denture are used in modern dental practice by those professionals who treat the teeth and associated tissues, and who artificially replace missing teeth. Applicant knows of no prior art patents which teach or disclose the invention to be hereinafter described and claimed, but a published monograph carrying the Copyright date of 1976 and entitled "Semi-Precision Attachment System for Subperiosteal Implants and Over-Dentures.", authored by the inventor shows and describes his initial and experimental attempt to reduce the invention to practice. As will later be more fully explained, the invention here disclosed is a substantial improvement over the system revealed in the monograph and provides an adroit solution to the problems encountered in the use and application of the disclosed attachment system. A copy of the monograph is attached to the letter of transmittal to assist the Examiner in his search of the prior art and his analysis of the claims.

SUMMARY OF THE INVENTION

The invention relates to a mehod and apparatus for attaching a removable denture to a natural or an implanted fixed root system. It is accordingly an object of the invention to provide an attachment structure for natural tooth roots or artificial implanted root systems.

It is another object of the invention to provide an attachment system for use with natural or implanted roots.

It is yet another object of the invention to provide a removable denture for use with a natural or implanted fixed root system which comprises at least one post suppported by the root system, an encapsulated resilient ring on the post and a denture fitted over the encapsulated ring.

It is a further object of the invention to provide a removable denture for use with a natural or implanted root system which comprises at least one post supported by the root system, a resilient ring embracing the post, an encapsulation enclosing the ring within its envelope, a metal cap on the encapsulation, and a denture surrounding the encapsulation.

BRIEF DESCRIPTION OF THE DRAWINGS

A detailed description of the invention will be made with reference to the accompanying drawings wherein like reference characters designate like, or corresponding, parts in the several figures.

DESCRIPTION OF PREFERRED EMBODIMENT

Figure 1:
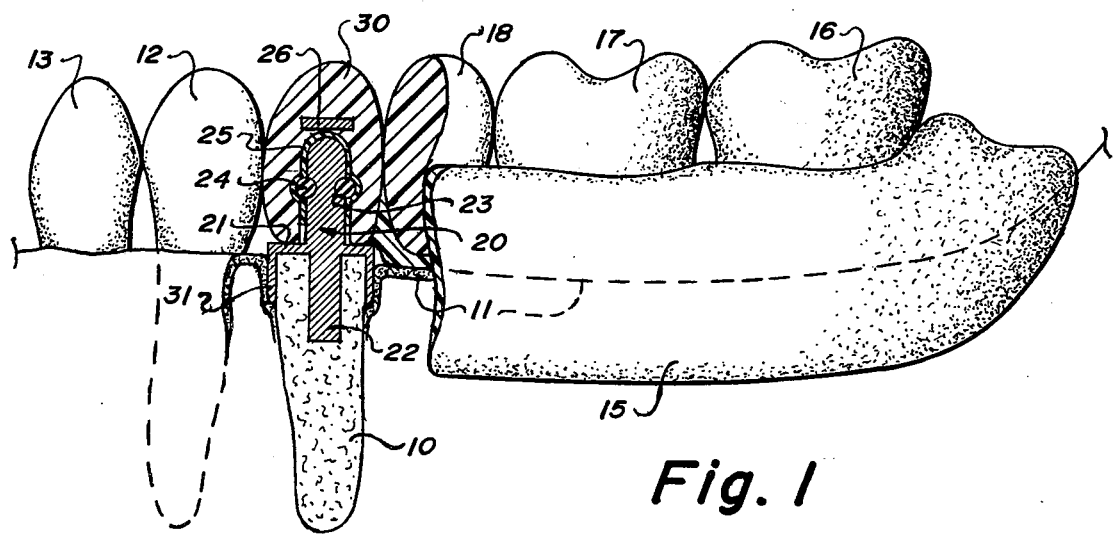
FIG. 1 is an elevation view partly in section showing the invention applied to a natural tooth root.

The following detailed description is of the best methods, and structures, and modes of carrying out the invention. The description is not to be taken in a limiting sense, but is made for the purpose of illustrating the general principles of the invention. The scope of the invention is defined by the appended claims. Reference is here made to U.S. Patent Office Disclosure Document Ser. No. 070968, received in the Patent Office on May 5, 1978 and which reveals evidence of the conception and actual reduction to practice of the invention disclosed and claimed herein.

The embodiment of the invention to be hereinafter described represents a substantial improvement over the sub-periostial implant system illustrated in the monograph referred to above, but can be used with the implant as a matter of professional judgement. Among other advantages, ease of processing and replacement can be recited.

Referring now to the drawing, reference character 10 designates a natural tooth root which has had its crown removed and shaped as by drilling and grinding. Reference character 11 designates the gum, and 12 and 13 indicate natural teeth remaining in the jaw bone of the person who is to receive the denture system. The saddle 15 of the denture carrying artificial teeth 16, 17 and 18 is shown straddling the gum tissue in the usual manner.

The interconnection between the denture system and the natural tooth root will now be described. A post 20 having a base 21 engaging the surface of root 10 has a depending portion 22 tightly fitted into a cavity drilled into the treated tooth root and has a circumferential kerf 23 formed therein. The post may be made from any suitable surgical or inert metal. A depending crown 31 surrounds the portion of the tooth root exposed to the oral cavity to lend lateral stability under stress. A resilient ring 24 is received in the kerf and ring is encapsulated in an organic, synthetic, or processed plastic envelope 25. A metal plate 26 engages the outer top surface of the encapsulating plastic envelope as there shown and for a purpose which will later be described. Artificial tooth 30 surrounds the assembly. The artificial tooth may be made from porcelain, gold, or from any of the numerous organic, synthetic, or processed plastic materials that are molded, cast, extruded or drawn into objects. It is readily seen that with the root drilled and the post portion 22 firmly fixed therein that the denture assembly consisting of saddle 15, teeth 16, 17, 18 and 30, and encapsulated resilient ring 24 and plate 26 may be easily fitted upon the post 20 for firm retention. The inherent resiliency of the ring, which may be of silicon rubber or any other suitable material, gives a high degree of circumferential retention and permits limited motion of the denture within the limits of its elasticity and ability to deform under the tension, compression and shearing stesses inherent in jaw working processes. In the unlikely event that the resilient ring needs to be replaced, the denture assembly is removed from the post (which remains on the root) and a small rotary cutting tool known in the art as a burr, approximately the diameter of the encapsulated ring, is used to grind out the old ring and plastic encapsulation. The metal plate 26 stops the end of the burr and prevents cutting of the artificial tooth 30. This is very important in the ring replacement function because once the proper spacing between upper and lower teeth has been achieved in the initial installation it must be retained for proper fit and bite.

Figure 2:
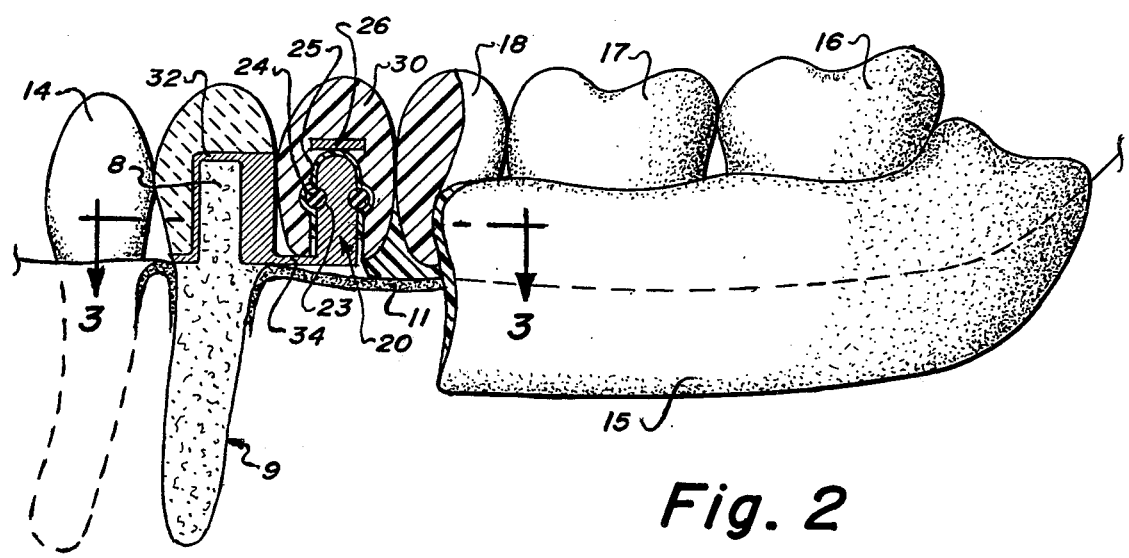
FIG. 2 is an elevation view partly in section showing the invention applied to a natural tooth in a cantilever arrangement.
Figure 3:
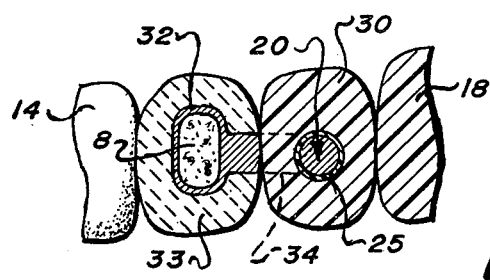
FIG. 3 is a plan view taken on lines 3—3 of FIG. 2.

Referring now to FIG. 2 and 3 wherein a cantilever member is used in the connecting structure, reference characters 15, 16, 17 and 18 indicate the denture saddle and artificial teeth, respectively. Reference character 14 refers to a natural tooth, and 9 designates a natural tooth having its upper portion removed, in part, as by grinding and drilling to form a boss 8 to receive cap 32. The cap may be of gold or any proper surgical inert material and, as is best seen in FIG. 3, is formed to correspond exactly with, and embrace, boss 8. Arm 34 extends laterally from the base of cap 32 and has formed thereon post 20 in a cantilever arrangement. As was described above in the species of FIG. 1, post 20 has a circumferential kerf 23 formed therein. A resilient ring 24 is received in the kerf and the ring is encapsulated in an organic, synthetic, or processed plastic envelope 25. Metal plate 26 engages the outer top surface of the encapsulating plastic envelope. Artificial tooth 30 surrounds the encapsulated ring assembly. Artificial tooth 33 covers boss 8 and cap 32.

After the preparation of the natural tooth and the fixing of the cap 32 on boss 8 the post 20 will receive the denture assembly consisting of saddle 15 carrying artificial teeth 16, 17, 18 and 30 which contains the encapsulated ring 24 and plate 26. The resiliency of the ring gives limited motion of the denture within the limits of its elasticity and ability to deform under the tension, compression and shearing stresses inherent in jaw motion and function. As described under the species of FIG. 1, if ring replacement is necessary or desirable, the denture assembly is removed from the post and a burr is used to remove the old ring. A new ring is processed in. The plate 26 insures against cutting of the surrounding artificial tooth material and maintains the proper spacing between upper and lower teeth to retain fit and bite.

It will be apparent to those skilled in the art that many changes may be made in the construction and arrangement of parts without departing from the scope of the invention as defined in the appended claims.

I claim:

1. A removable denture attachment system for use with a natural or implanted fixed root system which comprises in combination:
   (a) a post supported by said root system,
   (b) a resilient ring on said post,
   (c) an encapsulating envelope surrounding said ring and post, and
   (d) a denture surrounding said post, ring, and envelope.

2. The removable denture of claim 1 wherein the said post has formed therein a circumferential arcuate kerf to receive said resilient ring.

3. The removable denture of claim 2 including a metal plate fixed adjacent to the top end of said post and external to the encapsulating envelope.

4. The removable denture of claim 3 wherein the said post is metal and the said ring is a resilient material.

5. The removable denture of claim 4 wherein said post comprises a portion of a centilever structure extending laterally from the fixed root system.

6. The removable denture of claim 4 wherein said post is a truncated cone extending vertically from the fixed root system.

7. The removable denture of claim 4 comprising a cap embracing a portion of the root system and an arm extending laterally from said cap to support said post.

8. The removable denture of claim 4 wherein said resilient material is silicon rubber.

* * * * *